US007572842B2

(12) United States Patent
Zech et al.

(10) Patent No.: US 7,572,842 B2
(45) Date of Patent: Aug. 11, 2009

(54) AUTOMIXABLE PUTTY IMPRESSION MATERIAL

(75) Inventors: Joachim W. Zech, Kaufering (DE); Peter Bissinger, Diessen (DE); Henning Hoffmann, Windach (DE); Wolf Steiger, Lerchenweg (DE)

(73) Assignee: 3M ESPE AG, St. Paul ( * ) Notice: Subject to any disclaimer, the term of this patent is extended or adjusted under 35 U.S.C. 154(b) by 302 days.

(21) Appl. No.: 10/566,926

(22) PCT Filed: Jul. 30, 2004

(86) PCT No.: PCT/EP2004/008592

§ 371 (c)(1),
(2), (4) Date: Feb. 1, 2006

(87) PCT Pub. No.: WO2005/013925

PCT Pub. Date: Feb. 17, 2005

(65) Prior Publication Data

US 2006/0293469 A1 Dec. 28, 2006

(30) Foreign Application Priority Data

Aug. 1, 2003 (EP) .................................. 03017488

(51) Int. Cl.
*A61K 6/10* (2006.01)
*C08G 77/00* (2006.01)
*C08G 77/08* (2006.01)
*C08G 77/12* (2006.01)
*C08G 77/20* (2006.01)
*C08G 77/26* (2006.01)

(52) U.S. Cl. .................. 523/109; 528/31; 528/32; 528/38; 528/41; 528/15; 528/17

(58) Field of Classification Search .................. 525/477
See application file for complete search history.

(56) References Cited

U.S. PATENT DOCUMENTS

| | | | | |
|---|---|---|---|---|
| 3,715,334 | A | | 2/1973 | Karstedt |
| 3,775,352 | A | | 11/1973 | Leonard |
| 3,814,730 | A | | 6/1974 | Karstedt |
| 3,933,880 | A | | 1/1976 | Bergstrom et al. |
| 4,035,453 | A | * | 7/1977 | Hittmair et al. ............... 264/16 |
| 4,600,731 | A | * | 7/1986 | Louis et al. .................. 523/109 |
| 4,609,687 | A | * | 9/1986 | Schwabe et al. ............ 523/109 |
| 4,614,758 | A | * | 9/1986 | Schwabe et al. ............ 524/487 |
| 4,879,339 | A | * | 11/1989 | Yoshino et al. ............. 524/740 |
| 4,891,400 | A | * | 1/1990 | Schwabe et al. ............ 524/745 |
| 5,159,096 | A | | 10/1992 | Austin et al. |
| 5,220,033 | A | * | 6/1993 | Kamei et al. ................. 548/406 |
| 5,249,862 | A | | 10/1993 | Herold et al. |
| 5,286,105 | A | | 2/1994 | Herold et al. |
| 5,371,162 | A | * | 12/1994 | Konings et al. ............... 528/15 |
| 5,464,131 | A | | 11/1995 | Keller |
| 5,595,826 | A | * | 1/1997 | Gray et al. .................. 428/450 |
| 5,683,527 | A | * | 11/1997 | Angell et al. .................. 156/78 |
| 5,744,507 | A | * | 4/1998 | Angell et al. .................. 521/86 |
| 5,814,679 | A | * | 9/1998 | Eckberg et al. ............... 522/31 |
| 6,040,354 | A | * | 3/2000 | Hubner et al. ............... 523/109 |
| 6,121,362 | A | * | 9/2000 | Wanek et al. ............... 524/448 |
| 6,239,244 | B1 | * | 5/2001 | Stepp et al. .................... 528/15 |
| 6,335,413 | B1 | | 1/2002 | Zech et al. |
| 6,482,888 | B1 | * | 11/2002 | Ahn et al. ................... 524/588 |
| 6,512,037 | B1 | * | 1/2003 | Ahn et al. ................... 524/413 |
| 6,552,104 | B1 | * | 4/2003 | Hare .......................... 523/109 |
| 6,559,199 | B1 | * | 5/2003 | Pusineri et al. ............. 523/109 |
| 6,599,974 | B1 | * | 7/2003 | Bublewitz et al. ........... 524/588 |
| 2002/0147275 | A1 | | 10/2002 | Bublewitz et al. |
| 2002/0156186 | A1 | | 10/2002 | Bublewitz et al. |
| 2002/0197214 | A1 | * | 12/2002 | Bublewitz et al. ............. 424/53 |
| 2004/0028624 | A1 | | 2/2004 | Bublewitz |
| 2004/0110863 | A1 | * | 6/2004 | Zech et al. .................. 523/109 |

FOREIGN PATENT DOCUMENTS

| | | |
|---|---|---|
| EP | 0231420 B1 | 8/1987 |
| EP | 0268347 B1 | 5/1988 |
| EP | 0480238 B1 | 4/1992 |
| EP | 0492413 B1 | 7/1992 |
| EP | 0492412 B1 | 9/1992 |
| EP | 0615787 A1 | 9/1994 |
| EP | 0639622 B1 | 2/1995 |
| EP | 0730913 B1 | 9/1996 |
| EP | 1258239 A1 | 11/2002 |
| WO | WO 87/03001 | 5/1987 |
| WO | WO 96/08230 | 3/1996 |
| WO | WO 97/03110 | 1/1997 |
| WO | WO 97/37632 | 10/1997 |
| WO | WO 98/43727 | 10/1998 |

(Continued)

OTHER PUBLICATIONS

J. Burkhardt, Chemie u. Technologie d. Polysiloxane in "Silikone, Chemie u. Technologie", Vulkan Verlag, Essen, 1989, p. 23-37.

(Continued)

Primary Examiner—Randy Gulakowski
Assistant Examiner—Robert Loewe

(57) ABSTRACT

The present invention relates to a multicomponent automixable putty impression material, its components, mixtures of the components and a method for obtaining impressions with the multicomponent automixable putty impression material.

24 Claims, No Drawings

FOREIGN PATENT DOCUMENTS

| | | |
|---|---|---|
| WO | WO 98/44860 | 10/1998 |
| WO | WO 00/38619 | 7/2000 |
| WO | WO 01/92271 | 12/2001 |

OTHER PUBLICATIONS

Shih et al., Synthesis and Characterization of Polycarbonate/Polydimethylsiloxane Multiblock Copolymer Prepared From Dimethylsiloxane and Various Aromatic Dihydroxyl Monomers, J. Appl. Polym. Sci. 75 (2000) 545-552.

W. Noll, "Chemie u. Technologie d. Silikone", Verlag Chemie Weinheim 2. edition 1964, p. 162-206.

DIN 53018-1.

ISO 4823.

* cited by examiner

AUTOMIXABLE PUTTY IMPRESSION MATERIAL

The present invention relates to a multicomponent automixable putty impression material, its components, mixtures of the components and a method for obtaining impressions with the multicomponent automixable putty impression material.

Impression materials are generally used for securing a precise representation of oral hard and soft tissue to support and enable subsequent preparation of crowns, bridges, dentures and other oral prostheses. Several impression taking techniques like monophase shaping (one material at one time), sandwich technique (two materials at one time) and putty/wash technique (two materials subsequently at two different times) are known to the skilled person.

Generally, with this technique in a first step a putty material is used to obtain a supporting preimpression, which is subsequently in a second step refined by taking a second impression with a light body "wash" material. The kneadable putty material is cured as a preimpression material in the patients' mouth, trimmed after removing the preimpression from the mouth, and in a second subsequent step, is covered with a layer of a "wash" material and again cured in the patients' mouth in order to obtain a precise representation of oral hard and soft tissue. In the sandwich technique, this is done simultaneously during the pot life of the two materials, followed by simultaneously applying the two materials in the patients' mouth.

The preimpression material (putty) is often employed in the form of a kneadable putty material. When performing a process for taking an impression, the dentist usually relies on the preimpression material having a noticeable resistance upon contact between preimpression material and dental material with the advantage that a higher back pressure is generated in the impression tray when the impression is made. Such a resistance is desirable, since the danger of overpressing the material in the tray is limited. Since overpressing usually results in direct contact between the impression tray and one or more surfaces of dental material, information is lost and the impression may be useless.

One possibility for providing impression materials with a high resistance upon introduction into the oral cavity and onto the dental material the impression is to be taken from is to provide them with a high viscosity. Such high viscosities are, e.g., realized in putty preimpression materials. Such putty preimpression materials are generally provided as a 2K material with a base and a catalyst paste, where the base and the catalyst paste are taken from accordingly marked containers as lumps and the lumps are kneaded manually.

In employing polyorganosiloxanes as putty dental impression materials, however, a number of difficulties have arisen.

The above described dosage is usually effected with dosing spoons by means of which the kneadable material is removed from a container. This procedure is generally connected with a high expenditure of force. When the components are kneaded into a homogeneous compound, also a high expenditure of force is required. This procedure of dosing and mixing may involve a great number of errors, among which are wrong dosage and non-homogeneous mixing of the two components. Both factors can lead to insufficient cross-linking so that the precision of model making is no longer ensured. Additionally, kneading manually can introduce catalyst poisons into the material which may slow down or even partially prevent curing of the impression material, which can also be detrimental to the fidelity of the impression.

Many 2K-Automix dental silicone putty materials so far show limitations with regard to the consistencies that can be mixed in the widespread available mixing devices. In the field of impression materials both, in the Pentamix™ and in the Garant-mixing systems, consistencies not higher than heavy body viscosities can be mixed due to the limitation of the forces which are necessary to push and mix the pastes.

In order to overcome this problem, a number of so-called putty cartridge materials are known and commercially available. These materials are supposed to be processable with the above mentioned mixing systems and are offered as an alternative to kneadable putty materials. These materials have a light to heavy body consistency according to ISO 4823. Since these materials already exhibit a relatively high degree of cross-linking in the beginning of their pot life, generelly due to a rapid cross-linking reaction. As a consequence, the initial consistency of these materials is rapidly increased during the pot life so that their total pot life of the material, during which it can be successfully used is shortened. Upon exceeding of the pot life for a relatively short time or at unusually high ambient temperatures, the impression material may early form crosslinked, elastomeric domains or cure completely. Such an early curing or partial curing, however, may result in strained, distorted domains upon applying pressure un the material by the dentist so that the impressions are basically useless after removal from the oral cavity since the restoring forces of the elastomeric domains distort the impression.

In US 2002/0147275 a multi component system for making impressions comprising at least two components A and B is suggested. Component A contains at least one compound having at least two alkenyl groups, at least one compound having at least one alkynyl group and/or at least one Si—OH structural unit and at least one organohydrogenpolysiloxane and component B contains at least one condensation catalyst and/or condensation cross-linking agent and at least one hydrosilylation catalyst. According to the specification, the material cures in two steps. The suggested system is, however, insofar disadvantageous, as the combination of Si—OH compounds and Si—H-compounds together in the base compound can lead to a decreased shelf life due to self condensation of the Si—OH-compounds even under mild basic or acetic conditions, and the reaction of Si—OH-Groups and Si—H-groups can result in the formation of hydrogen during storage or the setting reaction.

In DE 101 16 223 it is suggested to prepare an automixable putty from two components A and B, wherein the mixing ratio of base and catalyst paste is 5:1 and the base paste has a Brookfield viscosity of 800 to 2000 Pas. The disclosed materials, however, usually require a modification of automixing systems. No two step condensation mechanism is described.

It has thus been the object of the present invention to provide automixer-suitable impression materials based on addition crosslinkable polydimethylsiloxanes which can be mixed and dispensed by automixing systems. It has further been an object of the invention to provide automixer-suitable impression materials based on addition crosslinkable polydimethylsiloxanes which, due to a two-step reaction mechanism, undergo a transition in viscosity to form a kneadable putty material with increased viscosity in a first reaction step after mixing.

The term "automixer-suitable impression material" in the context of the present invention relates to a multicomponent impression material which can be dispensed, for example, from a two-component disposable cartridge through a static mixer, e.g., of Mixpac (Keller EP 0 615 787 A1, EP 0 730 913 A1) or from tubular film bags in dual-chamber reusable cartridges through a dynamic mixer, e.g., in the "Mixstar" device of DMG-Mühlbauer (PCT/EP 98/01993 and PCT/EP 98/01858) or in the "Pentamix™" and "Pentamix™ 2" devices of 3M ESPE AG (EP-A-0 492 413 and EP-A-0 492 412).

It has been a further object of the present invention to provide an impression material which avoids the drawbacks known from prior art impression materials as set forth above. It has further been an object of the present invention to provide a method for the preparation of impressions from objects from which impressions are to be made utilizing the impression materials as described below. In particular, the object has been to provide a multi-component impression material which can be simply and readily mixed and is automixer-suitable, suitable for making impressions and undergoes transition to an elastic solid state.

It has now been found that a compositon containing a polyhydrogensiloxane, a vinyl terminated polydiorganosiloxane, a carbinol terminated or carboxyl terminated or amino terminated polydiorganosiloxane, a platinum catalyst and a condensation cure compound solve at least one of the above mentioned objects.

The present invention therefor relates to a composition comprising
a) at least one polydiorganosiloxane having at least two olefinically unsaturated groups as component (a),
b) at least one organohydrogenpolysiloxane as component (b),
c) at least one polydiorganosiloxane having at least one carbinol, carboxy or amino group as component (c),
d) at least one condensation cure compound as component (d) and
e) at least one addition cure precious metal catalyst as component (e).

A composition according to the present invention is designed to provide a multi-step curing reaction, which enables the composition to be prepared by an automixing-system, to be applied to an object in a putty-like consistency and to cure by an addition reaction mechanism to secure an impression of the surface of the object.

In order to be able to be cured by an addition reaction mechanism, the composition according to the present invention contains at least one polydiorganosiloxane having at least two olefinically unsaturated groups as component (a). Generally, according to the present invention all types of polydiorganosiloxanes having at least two olefinically unsaturated groups can be employed, as long as they are sufficiently reactive towards an organohydrogenpolysiloxane to yield crosslinked, cured preimpression materials which can serve the purpose of taking preimpressions of objects, preferably objects within the oral cavity of a human. Examples of polydiorganosiloxanes having at least two olefinically unsaturated groups include linear, branched or cyclic polydiorganosiloxanes with two or more vinyl groups. When a linear polydiorganosiloxane is used, such vinyl groups may generally be positioned anywhere along the polymer backbone or in one or more pendent groups. The vinyl groups may be positioned along the polymer backbone with even spacing or can be distributed randomly. While generally many types of polydiorganosiloxanes having two or more olefinically unsaturated groups will give good results when employed in the context of the present invention, the use of linear polydiorganosiloxanes with two to five olefinically unsaturated groups, preferably vinyl groups, preferably with two, three or four vinyl groups, is preferred.

Diorganopolysiloxanes with terminal triorganosiloxy groups of which at least one of the three organic groups is a vinyl group are preferred as component (a). Preferred diorganosiloxanes of this structure are represented by the following formula I:

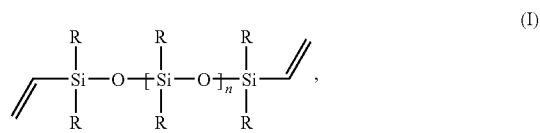

in which the radicals R each independently from another represent a linear or branched alkyl or fluoroalkyl group with 1 to 8 C-atoms or a cycloalkyl or aryl group with 6 to 14 C-atoms or an alkenyl group with 2 to 12 C-atoms.

The variable n is preferably chosen such that the viscosity lies between 4 and 200,000 mPas or between 6 and 100,000 mPas, preferably measured by a method as described in the text below. Preferred values for n are thus about 10 to about 2500 or about 20 to about 1500, depending on the types of substituents and the substitution pattern.

The radical R is preferably chosen such that it is free from aliphatic multiple bonds.

Preferably the radicals R can represent any non-substituted or substituted monovalent hydrocarbon group with 1 to 8 C-atoms, preferably 1 to 6 C-atoms. Generally, the radicals R can be equipped with all types of substituents that do not interfere with at least one of the remaining consituents of the composition and do not interfere with the curing reactions, e.g., fluorine substituents. The term "interfere" as used in the context of the present text relates to any influence of such a subsituent on at least one of the remaining consituents of the composition or the curing reactions, or both, which is detrimental to the properties of the hardened product. The term "detrimental" as used in the context of the present text relates to a change of properties of the precursors or the cured product that affects the usefulness of the precursors or the cured product related to the intended use of the precursors or the cured product in a negative manner.

In another preferred embodiment of the present invention at least 50% of the radicals R represent methyl groups. Examples for other radicals R that can be present in the organopolysiloxanes according to formula I are ethyl, propyl, isopropyl, n-butyl, tert.butyl, the pentyl isomers, the hexyl isomers, vinyl, allyl, 2-propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or hereroaromatic groups like phenyl or substituted phenyl groups. Examples for such molecules are described in U.S. Pat. No. 4,035,453, the disclosure of which, especially the disclosure of the latter document regarding the above mentioned molecules, their chemical constitution and their preparation, is expressly regarded as being part of the disclosure of the present document and is included herein by reference.

The preparation of molecules of the above mentioned formula I is generally known to the skilled person. The preparation of corresponding molecules can be achieved, e.g., according to standard procedures which are portrayed in W. Noll, "Chemie und Technologie der Silikone", Verlag Chemie Weinheim 2. edition 1964, pages 162-206 or J. Burghardt, Chemie und Technologie der Polysiloxane in "Silikone, Chemie und Technologie", Vulkan Verlag, Essen, 1989, pages 23-37.

Linear polydimethylsiloxanes of the above structure with the specified viscosity ranges for which the end groups consist of dimethylvinylsiloxy units and the other radicals R in the chain consist of methyl groups are particularly preferred.

Component (a), as described above, according to the present invention generally consists of one constituent. It can, however, be advantageous to have two or more constituents present in component (a). Such constituents can, for example, be labelled (a1) and (a2). It lies thus within the context of the present invention that component (a) consists of more than two different constituents, e.g., of 3, 4, 5, 6, 7, 8, 9 or 10 or more constituents which would then be labelled (a3), (a4), (a5), (a6), (a7), (a8), (a9) and (a10) up to $(a_n)$ for the $n^{th}$ constituent of n constituents overall.

If a component (a) consists of more than one constituents, at least two of the constituents constituting component (a) can differ in their viscosity, for example by a factor of at least 2. This means that in the material according to the invention, of the different types of organopolysiloxanes as constituents of component (a), at least (a1) and (a2) can have a different viscosity and the value for the viscosity of (a2) can be at least twice as high as the value for the viscosity of (a1) for the same type of viscosity measurement.

The term "constituents" as used herein with regard to the constituents of component (a) relates to organopolysiloxanes differing at least in their average weight molecular weight, related to their polydispersity after preparation, to a measurable extent. The present invention thus does not regard polymers of different chain lengths as obtained by a process for the preparation of one type of polymer within the achieved polydipersity of the chosen method as different constituents, under the proviso that the method of preparation results in a monomodal dispersion of polymer chain lengths.

The difference in viscosities can be higher than a factor of 2, e.g., a factor of 5, 10, 20, 30, 40, 50, 60, 70, 80, 90 or 100. It should be kept in mind that the values mentioned above relate to a factor for the difference in viscosities, not the viscosity values themselves.

It is thus also possible according to the present invention that component (a) comprises at least 3 constituents (a1), (a2) and (a3) with different viscosity values, (a1) having the lowest viscosity value and (a3) having the highest viscosity value.

Generally, all known types of viscosity measurements can be used according to the present invention, as long as the skilled person would consider this method applicable in the context of the present invention. A preferred method of measurement, however, is performed with Haake Rotovisco RV20 (spindle MV, measuring cup NV). The viscosity is measured at 23° C. After activation and rectification of the system, spindle MV is installed. Following, the material to be measured is filled into the measuring cup NV. Without undue delay, the spindle is lowered into the measuring cup NV. The spindle should be covered by a layer of max. 1 mm. The material to be measured is tempered for 20 min at 23° C. The measurement is started and the viscosity values (mPas) are recorded starting 20 s after the start of measurement. It has to be taken care of that at no time the measuring cup NV itself may rotate or move at all. A value for the viscosity is obtained in mPas. The above mentioned method of measurement corresponds to DIN 53018-1.

If component (a) consists of more than one constituent, the ratio of the amount of constituent with the lowest viscosity to the amount of constituent with the highest viscosity can be chosen relatively freely, depending on the desired properties of the precursors and the cured resin. It has, however, proven to be advantageous when ratio of the amount of constituent with the lowest viscosity to the amount of constituent with the highest viscosity is within a range of from about 1:20 to 20:1, especially 1:10 to 10:1 or 1:5 to 5:1. Good results have, e.g., been obtained with ratios of from about 1:3 to 3:1 or 1:2 to 2:1. It has furthermore proven adequate in some cases, when the amount of constituent with the highest viscosity is about equal to or higher than the amount of constituent with the lowest viscosity, resulting in a value of from about 0.9:1 to 3:1 for the ratio of the amount of constituent with the highest viscosity to the amount of constituent with the lowest viscosity. All ratios given are based on the weight of the constituents.

In order to be able to cure by an addition mechanism, a composition according to the present invention also contains at least one organohydrogenpolysiloxane as component (b). Component (b) is preferably an organohydrogenpolysiloxane with at least 3 Si-bonded hydrogen atoms per molecule. This organohydrogenpolysiloxane preferably contains 0.01 to 1.7 wt.-% silicon-bonded hydrogens. The silicon valencies which are not saturated with hydrogen or oxygen atoms are saturated with monovalent hydrocarbon radicals R which, however, should be free from ethylenically unsaturated bonds.

The hydrocarbon radicals correspond to the radicals R as defined above without the radicals having an ethylenically unsaturated bond. In a preferred embodiment of the present invention, at least 50%, preferably 100% of the hydrocarbon radicals in component (b) which are bonded to silicon atoms are methyl radicals. Such components are also described in the literature mentioned above with regard to structure and preparation.

Preferred organohydrogenpolysiloxanes contained in component (b) include polyalkyl-, polyaryl- and polyalkylaryl-, polyhaloalkyl-, polyhaloaryl- or polyhaloalkylarylsiloxanes. They may be in the form of oligomers or polymers in a linear, branched or cyclic form or as a QM resin and have at least one Si—H bond.

The above mentioned combination of components (a) and (b) is responsible for the last curing step, which is the addition curing reaction of the composition according to the present invention. In order to achieve an increase of viscosity after mixing the constituents of the composition according to the present invention which results in the desired increase of viscosity without irreversibly generating elastomeric domains in the material, the composition according to the invention contains at least one alkylsiloxane having at least one carbinol, carboxy or amino group as component (c).

Generally, as a component (c) all types of polyalkyxsiloxanes having at least one carbinol, carboxy or amino group or a mixture of two ore more of such groups can be employed as components (c). As long as they enable and support a first curing step in the compositions according to the present invention. It is generally possible and leads to good results in terms of an increase of viscosity in a first curing step, when a composition according to the present invention contains a component (c) with only one constituent, namely a polydiorganosiloxane having at least one carbinol, carboxy or amino group. It is, however, also possible that a composition according to the present invention contains an alkylsiloxane having at least one carbinol and at least one carboxy group or at least one carbinol and at least one amino group or at least one carboxy group and at least one amino group or at least one carbinol and at least one carboxy group and at least one amino group. It is also possible that a composition according to the present invention contains at least one alkylsiloxane having at least one carbinol and at least one alkylsiloxane having at least one carboxy group or at least one alkylsiloxane having at least one carbinol group and at least one alkylsiloxane having at least one amino group or at least one alkylsiloxane having at least one carboxy group and at least one alkylsiloxane having at least one amino group or at least one alkylsiloxane having at least one carbinol group and at least one alkylsiloxane having at least one carboxy group and at least one alkylsiloxane having at least one amino group.

In a preferred embodiment of the present invention component (c) contains at least one component of the formula

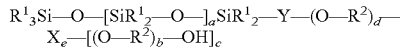
(II) or

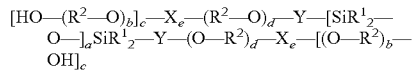
(III) or

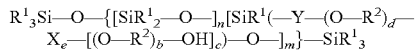
(IIIa) or (IIIb)

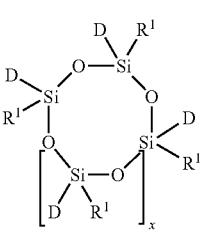

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or —Y—(O—$R^2$)$_d$—X$_e$—[(O—$R^2$)$_b$—OH]$_c$ with at least one residue —Y—(O—$R^2$)$_d$—X$_e$—[(O—$R^2$)$_b$—OH]$_c$ per molecule, $1 \leq a \leq 10.000$, $0 \leq b \leq 500$, $1 \leq c \leq 6$, $0 \leq d \leq 500$, e is 0 or 1, $0 \leq n \leq 500$, $0 \leq m \leq 100$ where m+n exceed 5 and x is 0, 1, 2, 3, 4, 5 or 6.

In another embodiment of the present invention component (c) contains at least one component of the formula

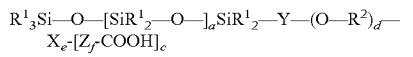
(IV) or

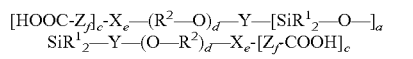
(V) or

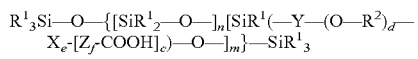
(Va) or (Vb)

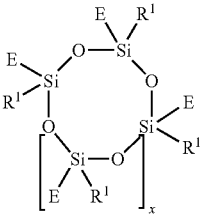

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 4 to 14 C-atoms, $R^2$ is a linear or branched alkylene group that may contain a carbonyl group with 1 to 8 C-atoms, E is $R^1$ or —Y—(O—$R^2$)$_d$—X$_e$-[Z$_f$-COOH]$_c$ with at least one residue —Y—(O—$R^2$)$_d$—X$_e$-[Z$_f$-COOH]$_c$ per molecule, $1 \leq a \leq 10.000$, $1 \leq c \leq 6$, $0 \leq d \leq 500$, e is 0 or 1, f is 0 or 1, $0 \leq n \leq 500$, $0 \leq m \leq 100$ where m+n exceed 5 and x is 0, 1, 2, 3, 4, 5 or 6.

In another embodiment of the present invention component (c) contains at least one component of the formula

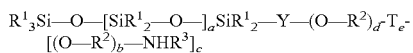
(VI) or

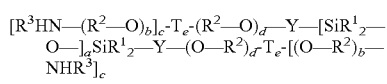
(VII) or

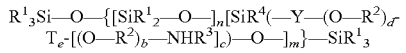
(VIIa) or (VIIb)

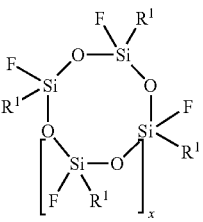

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, F is $R^1$ or —Y—(O—$R^2$)$_d$—T$_e$-[(O—$R^2$)$_b$—NHR$^3$]$_c$ with at least one residue —Y—(O—$R^2$)$_d$—T$_e$-[(O—$R^2$)$_b$—NHR$^3$]$_c$ per molecule, $R^3$ is a linear or branched alkyl or fluoroalkyl group with 1 to 8 C-atoms or a cycloalkyl or aryl group with 6 to 14 C-atoms or H, $R^4$ is $R^1$ or Methoxy or Ethoxy, $1 \leq a \leq 10.000$, $0 \leq b \leq 10.000$, $1 \leq c \leq 6$, $0 \leq d \leq 500$, e is 0 or 1, $0 \leq n \leq 500$, $0 \leq m \leq 100$ where m+n exceed 5 and x is 0, 1, 2, 3, 4, 5 or 6.

Preferred examples of the formula (c) have the following structures:

(c1) Polydimethylsiloxanes with Terminal or Pendant Carbinol Groups

The polydimethylsiloxanes are preferably linear but can also be cyclic or T-shaped. A preferred structure is for example $R^1_3Si$—O—[SiR$^1_2$—O—]$_a$SiR$^1_2$—Y—(O—R$^2$)$_d$—X$_e$—[(O—R$^2$)$_b$—OH]$_c$ or [HO—(R$^2$—O)$_b$]$_c$—X$_e$—(R$^2$—O)$_d$—Y—[SiR$^1_2$—O—]$_a$SiR$^1_2$—Y—(O—R$^2$)$_d$—X$_e$—[(O—R$^2$)$_b$—OH]$_c$ or $R^1_3Si$—O—{[SiR$^1_2$—O—]$_n$[SiR$^1$(—Y—(O—R$^2$)$_d$—X$_e$—[(O—R$^2$)$_b$—OH]$_c$)—O—]$_m$}—SiR$^1_3$ or

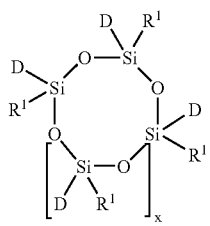

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or $—Y—(O—R^2)_d—X_e—[(O—R^2)_b—OH]_c$ with at least one residue $—Y—(O—R^2)_d—X_e—[(O—R^2)_b—OH]_c$ per molecule, $1 \leq a \leq 10.000$, $0 \leq b \leq 500$, $1 \leq c \leq 6$, $0 \leq d \leq 500$, e is 0 or 1, $0 \leq n \leq 500$, $0 \leq m \leq 100$ where m+n exceed 5 and x is 0, 1, 2, 3, 4, 5 or 6.

Also preferred are:

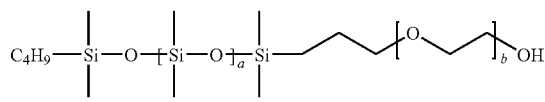

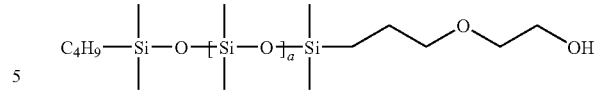

like MCR-C13 from Gelest (CAS: 67674-67-3)

like MCR-C12 and MCR-C22 from Gelest (CAS: 207308-30-3)

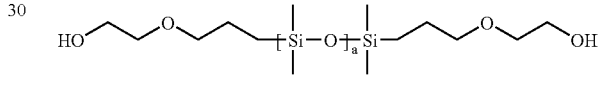

like Rhodorsil Oil 1647 V 60 and 1615 V 500 from Rhône-Poulenc (CAS: 58130-02-2)

like Tegomer H-Si 2111, 2311 and 2711 from Th. Goldschmidt

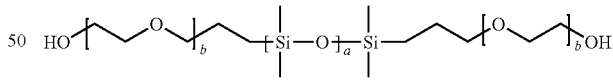

synthesized from allylglycol and Si—H terminated silicon oil

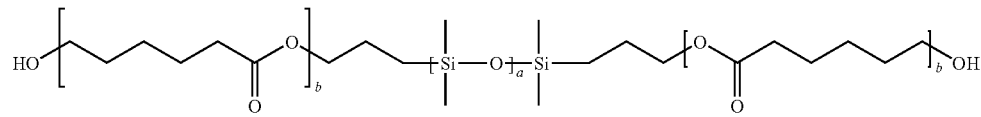

like DBL-C31 from Gelest (CAS: 120359-07-1) or Tegomer H-Si 6440 synthesized from allypolylglycol and Si—H terminated silicon oil according available from Hanse Chemie

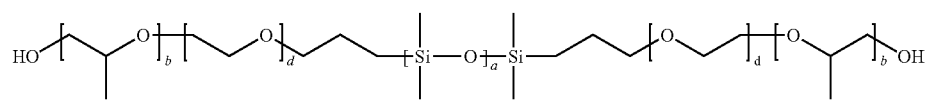

(EO+PO Adduct: Rhodorsil Oil 10646 from Rhône-Poulenc (CAS: 94469-32-6))

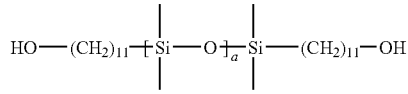

available from 10-undecene-1-ol and Si—H terminated silicon oil

synthesized from 2-butin-1,4-diol and Si—H terminated silicon oil

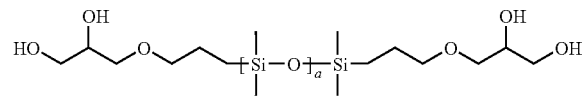

synthesized from Allylglycerol and Si—H terminated silicon oil, or from DMS-E01, E12 or E21 from Gelest (CAS: 104780-61-2)

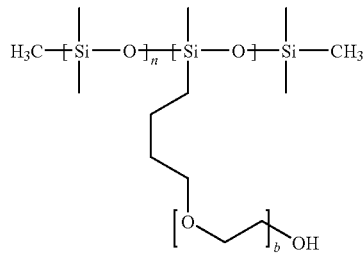

synthesized from Si—H pendant silicone oil and allyl polyglycole according to e.g. to U.S. Pat. No. 5,159,096,

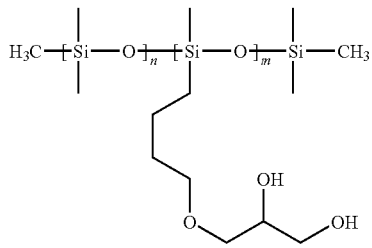

synthesized from Rhodorsil Oil 21620 from Rhône-Poulenc (CAS: 68440-71-1) and water

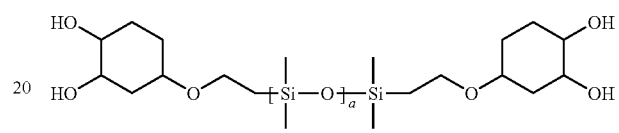

synthesized from VCHO and Si—H terminated silicon oil and addition of water

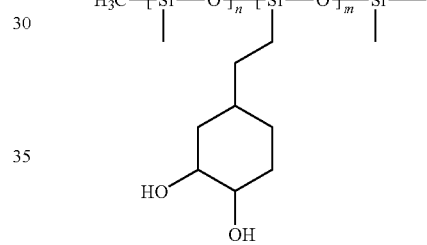

synthesized from Silicorelease Poly 200 or RCA 200 from Rhône-Poulenc (CAS: 67762-95-2) and water

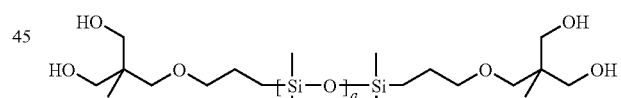

synthesized from trimethylolpropane-monoallyl ether and Si—H terminated silicon oil

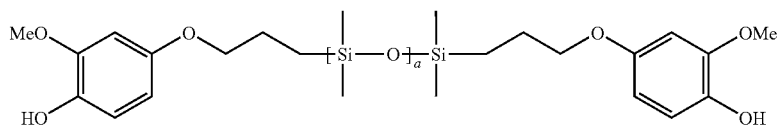

synthesized from eugenole and Si—H terminated silicon oil e.g. according to WO 97/03110 Example 4 or 5

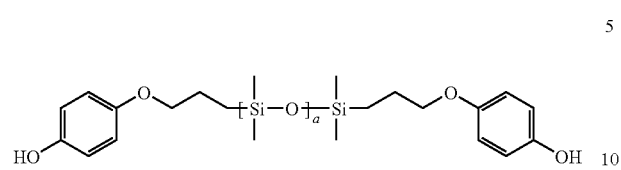

synthesized from allylphenole and Si—H terminated silicon oil, available from Shin Etsu Chemical Co., Ltd (Shih et al., J. Polym. Sci. 75 (2000) 545)

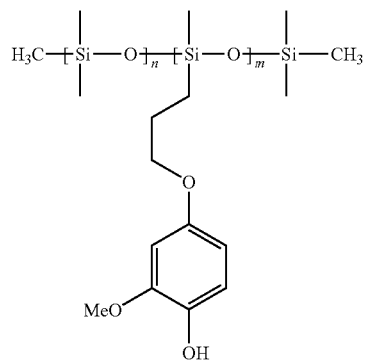

synthesized from eugenole and Si—H pendant silicon oil e.g. according to WO 97/03110 Example 1, 2 or 3

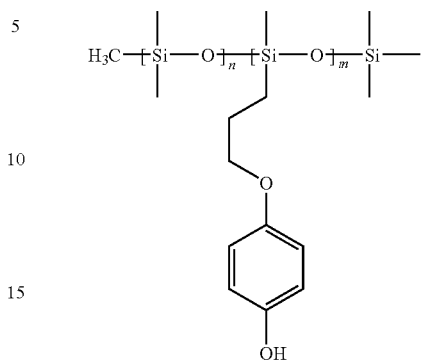

synthesized from allylphenole and Si—H pendant silicon oil

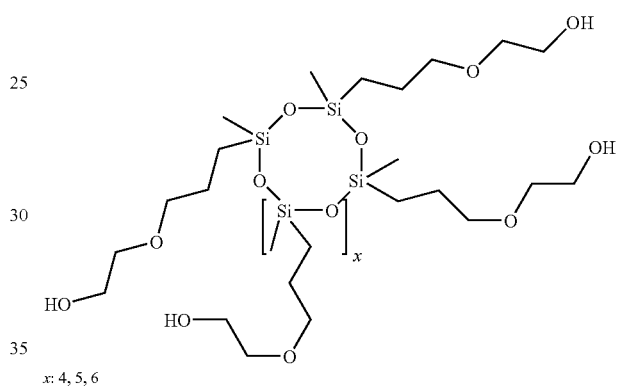

x: 4, 5, 6 synthesized from Si—H cyclics and allylglycol

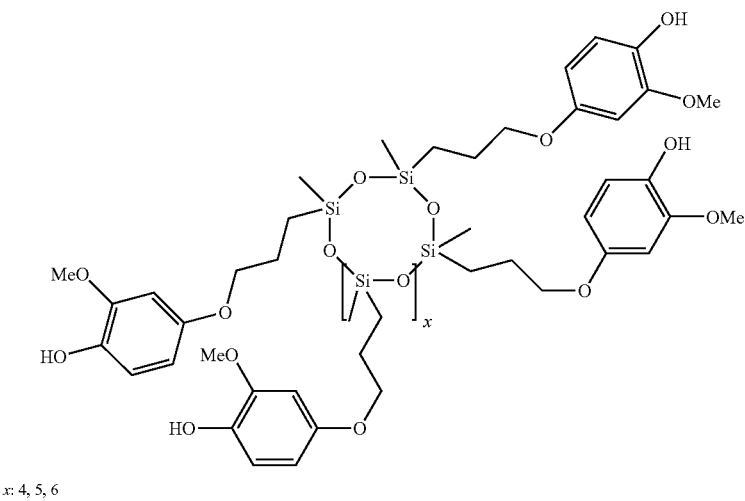

x: 4, 5, 6 synthesized from Si—H cyclics and eugenole

Especially preferred are also silicone oils with pendant carbinol groups like e.g. Silwet L-7200, L-7210, L-7220, L7230, L-7604, L-7644 or L-7657 of OSi.

(c2) Polydimethylsiloxanes with Terminal or Pendant Carboxy Groups

The polydimethylsiloxanes are preferably linear but can also be cyclic or T-shaped. A preferred structure is for example $R^1_3Si-O-[SiR^1_2-O-]_a SiR^1_2-Y-(O-R^2)_d-X_e-[Z_f-COOH]_c$ or $[HOOC-Z_f]_c-X_e-(R^2-O)_d-Y-[SiR^1_2-O-]_a SiR^1_2-Y-(O-R^2)_d-X_e-[Z_f-COOH]_c$ or $R^1_3Si-O-\{[SiR^1_2-O-]_n[SiR^1(-Y-(O-R^2)_d-X_e-[Z_f-COOH]_c)-O-]_m\}-SiR^1_3$ or

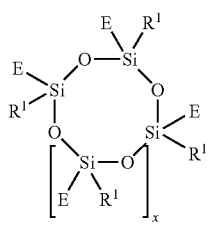

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, E is $R^1$ or $-Y-(O-R^2)_d-X_e-[Z_f-COOH]_c$ with at least one residue $-Y-(O-R^2)_d-X_e-[Z_f-COOH]_c$ per molecule, $1 \leq a \leq 10.000$, $1 \leq c \leq 6$, $0 \leq d \leq 500$, e is 0 or 1, f is 0 or 1, $0 \leq n \leq 500$, $0 \leq m \leq 100$ where m+n exceed 5 and x is 0, 1, 2, 3, 4, 5 or 6.

Also preferred are:

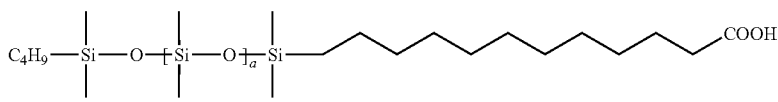

like MCR-B11 or CR-B16 from Gelest

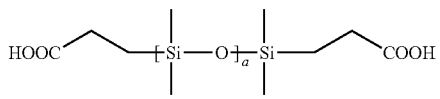

synthesized from methyl acrylate and Si—H terminated silicon oil and following saponification

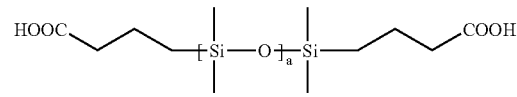

like DMS-B31 from Gelest

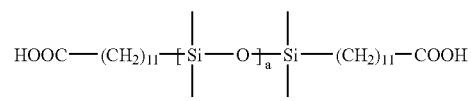

like DMS-B12 or B25 from Gelest

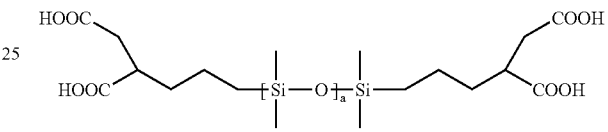

like DMS-Z11 from Gelest and the corresponding acid

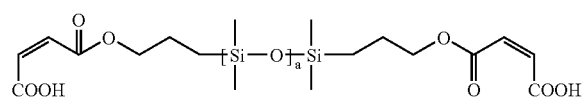

synthesized from carbinol terminated silicones and maleic anhydride

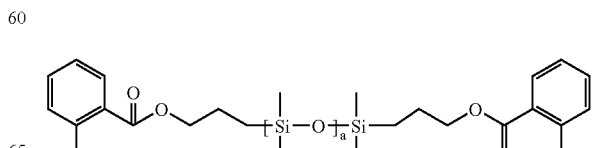

synthesized from carbinol terminated silicones and phthalic anhydride synthesized from Si—H cyclics allyl glycol and subsequent reaction with maleic anhydride

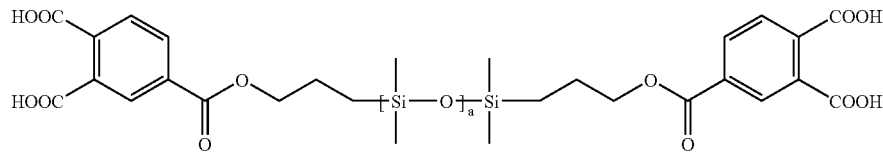

synthesized from carbinol terminated silicones and trimellitic anhydride chloride

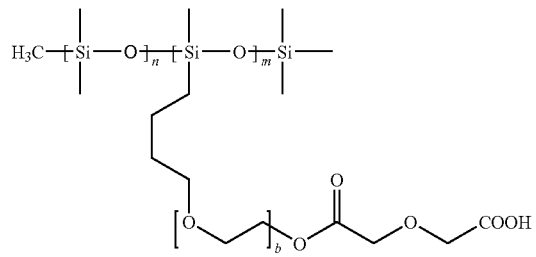

from carbinol pedant silicones and glycolic acid anhydride (c3) Polydimethylsiloxanes with Terminal or Pendant Amino Groups The polydimethylsiloxanes are preferably linear but can also be cyclic or T-shaped. A preferred structure is for example $R^1_3Si-O-[SiR^1_2-O-]_aSiR^1_2-Y-(O-R^2)_d-T_e-[(O-R^2)_b-NHR^3]_c$ or $[HR^3N-(R^2-O)_b]_c-T_e-(R^2-O)_d-Y-[SiR^1_2-O-]_aSiR^1_2-Y-(O-R^2)_d-T_e-[(O-R^2)_b-NHR^3]_c$ or $R^1_3Si-O-\{[SiR^1_2-O-]_n[SiR^4(-Y-(O-R^2)_d-T_e-[(O-R^2)_b-NHR^3]_c)-O-]_m\}-SiR^1_3$ or

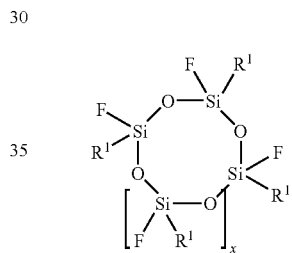

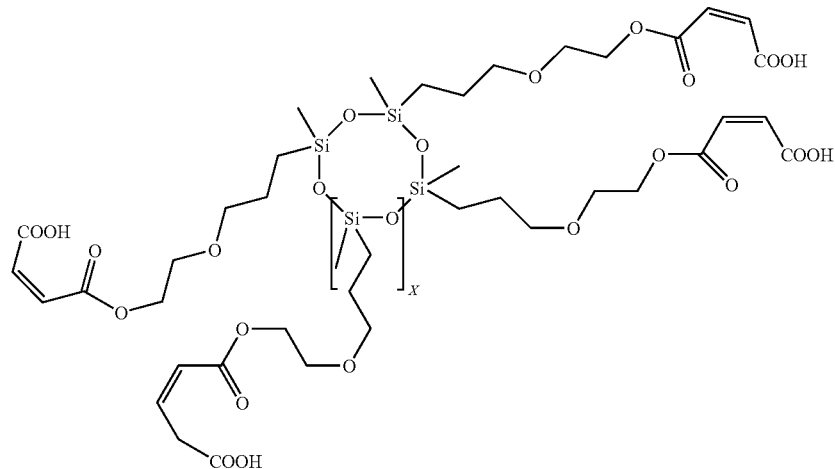

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, F is $R^1$ or —Y—(O—$R^2$)$_d$-T$_e$-[(O—$R^2$)$_b$—NHR$^3$]$_c$ with at least one residue —Y—(O—$R^2$)$_d$-T$_e$-[(O—$R^2$)$_b$—NHR$^3$]$_c$ per molecule, $R^3$ is a linear or branched alkyl or fluoroalkyl group with 1 to 8 C-atoms or a cycloalkyl or aryl group with 6 to 14 C-atoms or H $R^4$ is $R^1$ or Methoxy or Ethoxy, $1 \leq a \leq 10.000$, $0 \leq b \leq 500$, $1 \leq c \leq 6$, $0 \leq d \leq 500$, e is 0 or 1, $0 \leq n \leq 500$, $0 \leq m \leq 100$ where m+n exeed 5 and x is 0, 1, 2, 3, 4, 5 or 6.

Also preferred are:

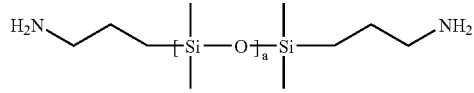

like PDMS Diamine 5k, 10k or 15k from 3M or Tegomer A-Si 2120 or 2130 from Th. Goldschmidt or DMS-A11, A12, A15, A25 or A32 from Gelest (CAS: 106214-84-0)

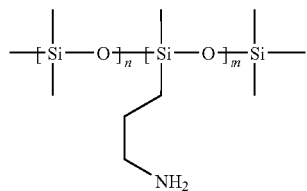

like Rhodorsil 21643 and 21644 from Rhône-Poulenc or AMS-132, 152, and 162 from Gelest (CAS: 99363-37-8)

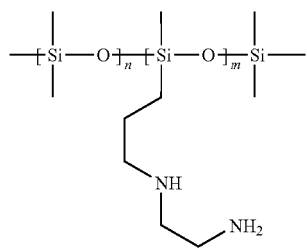

like Rhodorsil 21642 and 21637 from Rhône-Poulenc (CAS: 102782-92-3) or AMS-232 from Gelest (CAS: 71750-79-3)

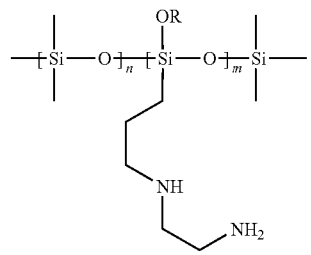

like Belsil ADM-Types of Wacker or ATM-1112 or 1322 from Gelest,

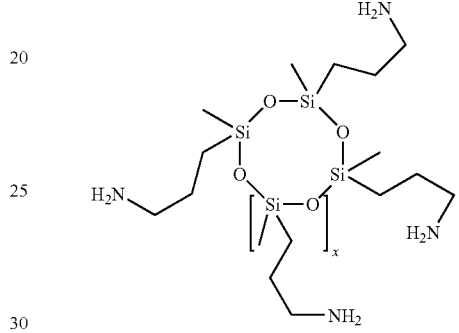

synthesized from Si—H cyclics acrylonitrile and subsequent reation with LiAlH$_4$.

In addition to the above described component (c), a composition according to the present invention contains a condensation cure compound as a component (d).

In the context of the present invention, the term "condensation cure compound" relates to a compound or a mixture of two or more compounds, which are able to cause a condensation reaction with or between substances which can undergo such a condensation reaction. The term "condensation cure compound", as used herein, does not necessarily relate to a compound which only acts as a catalyst within the classical meaning of the word but may also relate to a compound, which is consumed during the condensation reaction or otherwise takes part in the condensation process. The term "condensation cure compound", as used herein, can, however, also relate to a compound or a mixture of two or more compounds which can either act as a catalyst or can themselves take part in the condensation reaction as an active participant which is completely or partially consumed during the reaction, e.g., acts as a crosslinging agent.

Condensation cure compounds (d) preferably employed in the context of the present invention include aluminum alkoxides, antimony alkoxides, barium alkoxides, boron alkoxides, calcium alkoxides, cerium alkoxides, erbium alkoxides, gallium alkoxides, silicon alkoxides, germanium alkoxides, hafnium alkoxides, indium alkoxides, iron alkoxides, lanthanum alkoxides, magnesium alkoxides, neodymium alkoxides, samarium alkoxides, strontium alkoxides, tantalum alkoxides, titanium alkoxides, tin alkoxides, vanadium alkoxide oxides, yttrium alkoxides, zinc alkoxides, zirconium alkoxides, titanium or zirconium compounds, especially titanium and zirconium alkoxides, and chelates and oligo- and polycondensates of the above alkoxides, dialkyltin diacetate, tin(II)octoate, dialkyltin diacylate, dialkyltin oxide and double metal alkoxides. Double metal alkoxides are alkoxides containing two different metals in a particular ratio. In particular, the following are employed: titanium tetraethylate, titanium tetrapropylate, titanium tetraisopropylate, titanium tetrabutylate, titanium tetraisooctylate, titanium isopropylate tristearoylate, titanium triisopropylate stearoylate, titanium diisopropylate distearoylate, zirconium tetrapropylate, zirconium tetraisopropylate, zirconium tetrabutylate. In addition, titanates, zirconates and hafnates as described in DE 4427528 C2 and EP 0 639 622 B1 can be used. It is, however, preferred to employ condensation cure compounds (d) which are liquid at reaction temperature or which are soluble in the reacting compounds or both.

As component (e), the composition according to the present invention contains the catalyst which is able to initiate and/or catalyze the reaction between a polydiorganosiloxane with olefinically unsaturated groups or a mixture of two or more thereof and an organohydrogenpolysiloxane with at least 3 Si-bonded hydrogen atoms per molecule. Generally, all types of catalysts can be employed which are able to initiate and/or catalyze such a reaction, however, precious metal catalyst are commonly employed to fulfill this task. Component (e) is thus preferably a platinum complex which can be prepared from hexachloroplatinum acid by reduction with tetramethyldivinyidisiloxane. Such compounds are known to the skilled person. Any other platinum compounds which catalyze or accelerate addition cross-linking of silanes with ethylenically unsaturated double bonds are also suitable. Platinum-siloxane complexes as described, e.g. in U.S. Pat. Nos. 3,715,334, 3,775,352 and 3,814,730 are suitable, for example. The disclosure of these patents with regard to platinum complexes and their preparation is explicitly mentioned and expressly regarded as part of the disclosure of the present text.

The platinum catalyst is preferably used in quantities of 0.00005 to 0.05 wt.-%, particularly 0.0002 to 0.04 wt.-%, each calculated as elemental platinum and related to the overall weight of the material present with the components (a) to (e).

To control the reactivity of the addition reaction and to prevent premature curing, it may be advantageous to add an inhibitor which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the present invention. Examples of such inhibitors are acetylenic unsaturated alcohols such as 3-methyl-1-butyne-3-ol, 1-ethynylcyclohexane-l-ol, 3,5-dimethyl-1-hexyne-3-ol and 3-methyl-1-pentyne-3-ol. Examples of inhibitors based an vinyl siloxane are 1,1,3,3-tetramethyl-1,3-divinyl siloxane and poly-, oligo- and disiloxanes containing vinyl groups. The inhibitor is regarded as a part of component (e).

A composition according to the present invention can contain one or more adjuvants as a component (f).

As an adjuvant, the composition according to the present invention can contain an agent generally capable of giving a hydrophilic character to a composition or a hydrophilizing agent, which reduces the wetting angle of a drop of water or a water containing composition (e.g. a plaster suspension or the like).

The measurement of the wetting angle to determine the hydrophilicity of impression materials is e.g. described in DE 43 06 997 A, page 5, the contents of this document with regard to this method of measurement being expressly mentioned by reference and being regarded as part of the disclosure of the present text.

The hydrophilizing agents are preferably not equipped with reactive groups so that they are not incorporated into the polysiloxane network. Suitable hydrophilizing agents are preferably wetting agents from the group of hydrophilic silicone oils which are not capable of being covalently incorporated into the hardened polymer network. Suitable hydrophilizing agents are described in WO 87/03001 and in EP-B-0 231 420, the contents of which with regard to the hydrophilizing agents is expressly mentioned by reference and is regarded as part of the disclosure of the present invention.

Furthermore, ethoxylized fatty alcohols which are e.g. described in EP-B-0 480 238 are preferred. Furthermore, preferred hydrophilizing agents are polyether carbosilanes, e.g. known from WO 96/08230. Preferred are also the non-ionic perfluoralkylated surface-active substances described in WO 87/03001. Also preferred are the non-ionic surface-active substances which are described in EP-B-0 268 347, i.e. the nonylphenolethoxylates, polyethylene glycol-mono-und diesters, sorbitan esters as well as polyethylene glycol-mono- and diethers listed therein. The contents of the latter documents with regard to hydrophilizing agents and their preparation is expressly mentioned by reference and is regarded as part of the disclosure of the present invention.

The amounts of hydrophilizing agents used is 0 to about 10 wt.-%, relative to the overall weight of all components, preferably 0 to 2 wt.-% and particularly preferably 0 to 1 wt.-%. The wetting angle of a drop of water on the surface of a cured material according to the invention measured after 3 minutes, is preferably less than 60°, particularly preferably <50°, in particular <40°.

The compositions of the present invention also include a filler as an adjuvant, preferably a mixture of hydrophobic fillers. A wide variety of inorganic, hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6 μm); amorphous silicone dioxides, such as a diatomaceous earth (4-7 μm); and silanated fumed silica, such as Cab-o-Sil TS-530 (160-240 m$^2$/g), manufactured by Cabot Corporation.

The sizes and surface areas of the foregoing materials are controlled to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or silazides. Such fillers can be present in amounts of from about 5 to about 75 wt.-%, especially about 10 to about 70 or about 20 to about 60 wt.-% of the overall composition.

Among the fillers which can be used according to the present invention are non-reinforcing fillers such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers are also reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups.

One type of filler or also a mixture of at least two fillers can be used. The particle distribution is preferably chosen such that there are no fillers with particle sizes of more than 50 μm.

The overall content of fillers is in the range from 10 to 90%, preferably 30 to 80%, with regard to the overall composition.

A combination of reinforcing and non-reinforcing fillers may be employed. In this respect, the quantity of reinforcing fillers ranges from about 0.01 to about 10 wt.-%, in particular from about 0.05 to about 5 wt.-%, with regard to the overall composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Particularly preferred non-reinforcing fillers are quartzes, cristobalites and sodium aluminium silicates which can be surface-treated. The surface treatment can generally be carried out with the same methods as described in the case of the strengthening fillers.

Furthermore, the dental materials according to the invention can optionally contain adjuvants such as plasticizers, pigments, anti-oxidizing agents, release agents and the like. For example, a chemical system may be employed to diminish the presence or degree of hydrogen outgassing which may be typically generated as a result of the vinyl polymerization. The composition thus may comprise a finely divided platinum or palladium metal or palladium compound (see e.g. WO 97/37632) that scavenges for and takes up such hydrogen. The Pt or Pd metal or Pd compound may be deposited upon a substantially insoluble salt having a surface area of between about 0.1 and 40 m$^2$/g. Suitable salts are barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones.

The materials according to the invention contain such additives in quantities of 0 to about 2 wt.-%, preferably 0 to about 1 wt.-%.

A composition according to the present invention can also contain inert carrier materials. Such inert carrier materials preferably include mineral oils, branched hydrocarbons, vaseline, silicon oils, esters, phthalic acid esters, acetyltributyl citrate, polyalkylene oxides and polyesters and their copolymers.

In a preferred embodiment of the present invention, a composition according to the present invention contains the following components in the following amounts:
a) 2.5 to 40 weight percent of component (a),
b) 0.2 to 10 weight percent of comcomponent (b),
c) 0.5 to 8 weight percent of component (c),
d) 0.1 to 7 weight percent of component (d),
e) 0.0005 to 0.05 weight percent of component (e), calculated as elemental Pt, and
f) 31 to 96.65 weight percent adjuvants as component (f), wherein the components add up to 100 weight percent.

For reasons of storage stability, it can be preferable to formulate the materials in a two-component dosage form at least comprising components A and B, in which the component A is present in a so-called base paste. The component B is present physically separated from the base paste in the form of a so-called catalyst paste.

The present invention thus also relates to a two component system comprising components A and B, wherein component A comprises
a) at least one polydiorganosiloxane having at least two olefinically unsaturated groups as component (a),
b) at least one organohydrogenpolysiloxane as component (b),
c) at least one alkylsiloxane having at least one carbinol, carboxy or amino group as component (c), and component B comprises
d) at least one condensation cure catalyst as component (d) and
e) at least one addition cure precious metal catalyst as component (e).

In a preferred embodiment acording to the present invention, in the two component system component (c) contains at least one compound of the formula II, III, IIIa, IIIb, IV, V, Va, Vb, VI, VII, VIIa or VII b or a mixture of two or more thereof, wherein X is a linear or branched hydrocarbon or an aryl residue that may contain an oxygen atom and/or an ether group with 6 to 14 C-atoms and a valency of c, T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 4 to 14 C-atoms, $R^2$ is a linear or branched alkylene group that may contain a carbonyl group with 1 to 8 C-atoms, D is $R^1$ or —Y—(O—$R^2$)$_d$—X$_e$—[(O—$R^2$)$_b$—OH]$_c$ with at least one residue —Y—(O—$R^2$)$_d$—X$_e$—[(O—$R^2$)$_b$—OH]$_c$ per molecule, E is $R^1$ or —Y—(O—$R^2$)$_d$—X$_e$-[Z$_f$-COOH]$_c$ with at least one residue —Y—(O—$R^2$)$_d$—X$_e$-[Z$_f$-COOH]$_c$ per molecule, F is $R^1$ or —Y—(O—$R^2$)$_d$-T$_e$-[(O—$R^2$)$_b$—NHR$^3$]$_c$ with at least one residue —Y—(O—$R^2$)$_d$-T$_e$-[(O—$R^2$)$_b$—NHR$^3$]$_c$ per molecule, $R^3$ is a linear or branched alkyl or fluoroalkyl group with 1 to 8 C-atoms or a cycloalkyl or aryl group with 6 to 14 C-atoms or H, $R^4$ is $R^1$ or Methoxy or Ethoxy, $1 \leq a \leq 10.000$, $1 \leq c \leq 6$, $0 \leq d \leq 500$, e is 0 or 1, f is 0 or 1, $0 \leq n \leq 500$, $0 \leq m \leq 100$ where m+n exceed 5 and x is 0, 1, 2, 3, 4, 5 or 6.

In a further preferred embodiment component A of a two component composition according to the present invention contains the following components in the following amounts:
a) 8 to 35% by weight of component (a),
b) 1 to 10 weight percent of component (b),
c) 0.5 to 10 weight percent of component (c) and
d) 55 to 90.5 weight percent of adjuvants, wherein the components add up to 100 weight percent.

In a further preferred embodiment component B of a two component composition according to the present invention contains the following components in the following amounts:
a) 0.5 to 10 weigt percent of component (d),
b) 0.0005 to 0.05 weight perent of component (e), based on elemental Pt, and
c) 85 to 99.4 weight percent of adjuvants as component (e, wherein the components add up to 100 weight percent.

Preferably, a composition according to the present invention, contains at least one adjuvant selected from the group consisting of inert carrier materials, inhibitors, fillers, pigments or solvents.

The present invention thus also relates to a material according to the present invention, wherein said material is present in the form of a base paste and a catalyst paste physically separated from it, the whole components (a), (b) and (c) being present in the base paste and the whole components (d) and (e) being present in the catalyst paste and the remaining components (f) being optionally distributed in the two pastes.

The adjuvants (f) can be present in their full amount in the catalyst or base paste, where it is preferable that a part of each of the respective components are present in the catalyst paste B and a part in the base paste A.

It it further preferred, when the base paste A has an ISO-consistency of about 28 to 45 mm, preferably of about 33 to about 41 mm and catalyst paste B has an ISO-consistency according to ISO 4823 of about 30 to about 38 mm, especially about 33 to about 37 mm.

The volume ratios of catalyst and base pastes can be 10:1 to 1:10. Particularly preferred volume ratios of base paste:catalyst paste are about 1:1 and about 5:1 (5 parts base paste:1 part catalyst paste). In the case of a volume ratio of 1:1, the components (a) to (f) can be distributed as follows as base and catalyst paste:

TABLE 1

| Component | Base paste A (wt.-%) | Catalyst paste (wt.-%) | Total in base and catalyst paste (wt.-%) |
|---|---|---|---|
| (a) | 8 to 35 | — | 8 to 35 |
| (b) | 1 to 10 | — | 1 to 30 |
| (c) | 0.5 to 10 | — | 0.5 to 10 |
| (d) | — | 0.5-10 | 0.5 to 10 |
| (e) | — | 0.1-5 | 0.1 to 5 |
| (f) | 55-90.5 | 85-99.4 | 55-89.9 |

With a volume ratio of 1:5 to 5:1, both pastes can be filled into tubular film bags and later, shortly before use, can be mixed using a mixing and dosing device such as PENTA-MIX™ (3M ESPE AG).

A dosage in the form of double-chambered cartridges or capsules is also possible. Due to the initial low viscosity of the baser and catalyst pastes also hand mixing, e.g., by spatula or the like is possible.

The compounds according to the present invention are generally obtainable by mixing the respective components in the amounts given above.

The present invention thus also relates to a method for the preparation of a composition, wherein a) at least one polydiorganosiloxane having at least two olefinically unsaturated groups as component (a), b) at least one organohydrogenpolysiloxane as component (b), c) at least one alkylsiloxane having at least one carbinol, carboxy or amino group as component (c), d) at least one condensation cure catalyst as component (d) and e) at least one addition cure precious metal catalyst as component (e), based on elemental Pt, and, optionally, f) adjuvants as component (f)

are thoroughly mixed.

The materials according to the present invention are particularly suitable as dental preimpression materials or preliminary impression materials or as bite registration materials or as tray materials for the sandwich technique.

The cured compositions according to the invention have an end hardness of preferably shore hardness A≧35, preferably ≧45, particularly preferably shore hardness A≧60 or ≧65 with excellent low processing viscosity during mixing.

It is furthermore preferred when the ISO-consistency according to ISO 4823 of the mixed composition according to the present invention is between about 15 and about 35 mm, preferably between about 17 and about 33 mm.

The present invention also relates to a method for the preparation of impressions of an object, wherein the surface of the object is brought into contact with a composition according to the present invention or with a mixture of components A and B of a two component mixture according to the present invention or with a composition prepared according to the present invention. It is preferred, when the object is a surface within the oral cavity of a human.

The present invention also relates to the use of at least one alkylsiloxane having at least one carbinol, carboxy or amino group for the preparation of a composition for taking impressions of an object, preferably the object is within the oral cavity of a human.

The composition according to the present invention allows for a precise reconstruction of objects and their surfaces, especially of dental objects like dental fillings or dental prosthesis.

The present invention thus also relates to a dental filling or adental prosthesis, obtained from an impression taken with a composition according to the present invention.

The invention is explained in more detail by way of examples.

EXAMPLES

Synthesis of Carbinol-Silicones

Substance 1

318 mg of Pt/C (10% Pt) were dispersed in 250 ml Toluene and 7.6 g of 2-Allyloxy-ethanol (74.9 mmol). 500 g α,ω-Si—H terminated Silicone (34.0 mmol) are added within 3 h under reflux. The mixture is refluxed until SiH absorption in the IR spectrum at ~2100 cm$^{-1}$ disappeared. After filtration and removal of solvent 449 g (88.5%) of a clear viscous polymer remains. Viscosity: 1.0 Pa*s, OH-eqiv.: 9070.

Substance 2

639 mg of Pt/C (10% Pt) were dispersed in 300 ml Toluene and 10.0 g of 3-Allyloxy-1,2-propandiol (74.9 mmol). 500 g α,ω-Si—H terminated Silicone (34.0 mmol) are added within 5 h under reflux. The mixture is refluxed until SiH absorption in the IR spectrum at ~2100 cm$^{-1}$ disappeared. After filtration and removal of solvent 475 g (93%) of a clear viscous polymer remains. Viscosity: 1.9 Pa*s, OH-eqiv.: 4500.

Substance 3

583.7 mg of Pt/C (10% Pt) were dispersed in 500 ml Toluene and 29.6 g of 3-Allyloxy-1,2-propandiol (224 mmol). 120.6 g α,ω-Si—H terminated Silicone (51.7 mmol) are added within 5 h under reflux. The mixture is refluxed until SiH absorption in the IR spectrum at ~2100 cm$^{-1}$ disappeared. After filtration and removal of solvent 123.5 g (100%) of a clear viscous polymer remains. Viscosity: 1 Pa*s, OH-eqiv.: 650.

Substance 4

102.6 mg of Pt/C (10% Pt) were dispersed in 100 ml Toluene and 2.3 g of Allyl alcohol (40.1 mmol). 100 g α,ω-Si—H terminated Silicone (DMS-H21; 16.7 mmol) are added within 1 h under reflux. The mixture is refluxed until SiH absorption in the IR spectrum at ~2100 cm$^{-1}$ disappeared. After filtration and removal of solvent 100.9 g (99%) of a clear viscous polymer remains. GPC: $M_w$=8500; OH-eqiuv.: 2860.

Substance 5

54.3 mg of Pt/C (10% Pt) were dispersed in 50 ml Toluene and 4.26 g of 10-Undecen-1-ol (25 mmol). 50 g α,ω-Si—H terminated Silicone (DMS-H21; 8.33 mmol) are added within 1 h under reflux. The mixture is refluxed until SiH absorption in the IR spectrum at ~2100 cm$^{-1}$ disappeared. After filtration and removal of solvent 52.8 g (100%) of a clear viscous polymer remains. GPC: $M_w$=5200; OH-eqiuv.: 2504.

Substance 6

23.1 mg of Hexachloroplatinic acid Pt were dispersed in 200 ml Toluene and 60.1 g of 5-Hexen-1-ol (600 mmol). At 50° C. 26.1 g 1,1,3,3-Tetramethyldisiloxane (200 mmol) are added dropwise. The mixture is heated until SiH absorption in the IR spectrum at ~2100 cm$^{-1}$ disappeared. After removal of catalyst and solvent 62.2 g (90%) of a clear mobile liquid remains. After distillation at reduced pressure: OH-eqiuv.: 180.

Substance 7

320 mg of Pt/C (10% Pt) were dispersed in 600 ml Toluene and 20.0 g of 5-Hexen-1-ol (200 mmol). 300 g α,ω-Si—H terminated Silicone (DMS-H21; 50 mmol) are added within 1 h under reflux. The mixture is refluxed until SiH absorption in the IR spectrum at ~2100 cm$^{-1}$ disappeared. After filtration and removal of solvent 309.7 g (100%) of a clear viscous polymer remains. GPC: $M_w$=7900; OH-eqiuv.: 2130.

Substance 8

Under argon 8.54 g 9-Borabicyclononane (70 mmol) are dissolved in 150 ml THF. 245.4 g α,ω-Si-Vinyl terminated Silicone (VS 200, 31.9 mmol) were added at room temperature. The mixture was stirred over night. A mixture of 50 ml Ethanol 18 ml 4 N aqueous NaOH were added. 24 g 30% $H_2O_2$ (212 mmol) was added dropwise. After common workup and seperation of the product 200 g (81%) of a viscous polymer remained. OH-equiv.: 7630.

Substance 9

31 g of Caprolactone (276 mmol), 40 g Substance 3 (15.3 mmol) and 0.6 ml Dibutyltin dilaurate were charged into a vessel and heated 1 hour to 75° C., 5 hours to 140° C. and 1 hour to 180° C. under nitrogen. Upon cooling overnight the reaction mixture congeals. After removal of catalyst and unreacted Caprolactone 65 g waxy white solid remain. Fp.: 50-60° C., OH-Equiv.: 1060.

Synthesis of Carboxy-Silicones

Substance 10

644 mg of PVC (10% Pt) were dispersed in 300 ml Toluene and 13.8 g of 11-Undecenoic acid (74.8 mmol). 500 g α,ω-Si—H terminated Silicone (34.0 mmol) are added within 4 h under reflux. The mixture is refluxed until SiH absorption in the IR spectrum at ~2100 cm$^{-1}$ disappeared. After filtration and removal of solvent and thin film evaporation 340 g (66.7%) of a clear viscous polymer remains. Viscosity: 3.3 Pa*s.

Substance 11

200 g (11.0 mmol) of Substance 1 and 3.2 g (33.1 mmol) od Maleic anhydride were heated together in an Erlenmeyer flask at 70° C. for a sufficient time. Excess of maleic anhydride is removed by filtration. A clear viscous product is obtained (184 g, 90.6%). Viscosity: 2.0 Pa*s.

Base pastes and catalyst pastes were prepared using the following compositions:

Example A (with Carbinol Terminated Polydimethylsiloxane)

Base Paste:

| Compound | Amount [%-weight] |
| --- | --- |
| Organohydrogenpolysiloxane (0.16 wt. % $H_2$) | 4.00 |
| Vinyl-terminated Polydimethylsiloxane, 2000 cSt | 17.00 |
| Vinyl-terminated Polydimethylsiloxane, 200 cSt | 11.50 |
| Polydimethylsiloxane carbinol-terminated (Substance 2) | 3.00 |
| Cristobalit filler | 62.49 |
| Hydrophobic fumed silica | 2.00 |
| Blue Pigment | 0.01 |

Catalyst Paste:

| Compound | Amount [%-weight] |
| --- | --- |
| Mineral oil | 17.95 |
| Vaseline | 16.45 |
| Hydrophobic fumed silica | 4.50 |
| Yellow Pigment | 0.10 |
| Cristobalit filler | 57.50 |
| Platinum Catalyst Solution | 1.50 |
| Tetrakis(isopropoxy)titanate | 2.00 |

Example B (with Carboxyl Terminated Polydimethylsiloxane)

Base Paste:

| Compound | Amount [%-weight] |
| --- | --- |
| Organohydrogenpolysiloxane (0.16 wt. % $H_2$) | 4.50 |
| Vinyl-terminated polydimethylsiloxane, 2000 cSt | 15.00 |
| Vinyl-terminated polydimethylsiloxane, 200 cSt | 12.00 |
| Polydimethylsiloxane carboxyl-terminated (Substance 11) | 4.00 |
| Cristobalit filler | 52.49 |
| Silica filler | 12.00 |
| Blue pigment | 0.01 |

Catalyst Paste:

| Compound | Amount [%-weight] |
| --- | --- |
| Mineral oil | 16.42 |
| Vaseline | 15.92 |
| Hydrophobic fumed silica | 4.49 |
| Yellow Pigment | 0.10 |
| Cristobalit filler | 56.59 |
| Platinum Catalyst Solution | 1.50 |
| Tetrakis(isopropoxy)titanate | 4.99 |

Example C (with Amino Terminated Polydimethylsiloxane)

Base Paste:

| Compound | Amount [%-weight] |
|---|---|
| Organohydrogenpolysiloxane (0.16 wt. % $H_2$) | 4.50 |
| Vinyl-terminated Polydimethylsiloxane, 2000 cSt | 13.00 |
| Vinyl-terminated Polydimethylsiloxane, 200 cSt | 12.00 |
| Polydimethylsiloxane aminopropyl-terminated ($M_w$ about 13,000) | 6.00 |
| Cristobalit filler | 52.49 |
| Silica filler | 12.00 |
| Blue Pigment | 0.01 |

Catalyst Paste:

| Compound | Amount [%-weight] |
|---|---|
| Mineral oil | 16.42 |
| Vaseline | 15.92 |
| Hydrophobic fumed silica | 4.49 |
| Yellow Pigment | 0.10 |
| Cristobalit filler | 56.59 |
| Platinum Catalyst Solution | 1.50 |
| Tetrakis(isopropoxy)titanate | 4.99 |

Example D (with Carbinol Terminated Polydimethylsiloxane)

Base Paste:

| Compound | Amount [%-weight] |
|---|---|
| Organohydrogenpolysiloxane (0.16 wt. % $H_2$) | 4.00 |
| Vinyl-terminated Polydimethylsiloxane, 2000 cSt | 28.50 |
| Polydimethylsiloxane amino-terminated (substance 2) | 2.00 |
| Cristobalit filler | 63.49 |
| Silica filler | 1.50 |
| Blue Pigment | 0.01 |

Catalyst Paste:

| Compound | Amount [%-weight] |
|---|---|
| Mineral oil | 20.00 |
| Vaseline | 11.40 |
| Hydrophobic fumed silica | 4.50 |
| Yellow Pigment | 0.10 |
| Cristobalit filler | 57.50 |
| Platinum catalyst solution | 1.50 |
| Tetrakis(isopropoxy)titanate | 1.50 |
| Polydimethylsiloxane (50 cSt) | 3.50 |

As a Platinum catalyst solution a solution of a Platinum catalyst containing 1.3 weight-% of elemental Pt complexed by 1,1,3,3-tetramethyldivinylsiloxane in silicone oil (50 mPas) is used.

After mixing these pastes in a volume ratio of base:catalyst of 5:1 (v/v) the material showed a malleable putty consistency. The mixed pastes cured after about 5-8 minutes at room temperature to a rubber showing a high Shore hardness A.

ISO-consistency of the base paste, catalyst paste and of the mixed paste were measured to demonstrate the increase of consistency caused by the condensation cure system after mix of base and catalyst paste.

|  | Example A | Example B | Example C | Example D |
|---|---|---|---|---|
| ISO-consistency of base paste | 36 | 40 | 39 | 37 |
| ISO-consistency of catalyst paste | 34 | 36 | 36 | 44 |
| ISO-consistency of mixed paste | 19 | 18 | 25 | 24 |
| Shore A after 24 h | 70 | 75 | 65 | 60 |
| Setting time (Shawbury-Curometer, 23° C.) | 6.3 min | 8.0 min | 8.0 min | 6.00 min |

All above mentioned consistency data were created by handmixing of the pastes (examples A, B and C), the paste of example D was obtained by mixing in a Pentamix® 2 device (3M ESPE AG, Germany).

Mixed pastes show a puffy-like consistency although the single pastes do not. Two minutes after mixing the consistency was still malleable and had not yet set. This shows that the increase in viscosity is a result of the condensation system which acts very quickly.

The invention claimed is:

1. A dental impression composition comprising:
   a) at least one polydiorganosiloxane having at least two olefinically unsaturated groups as component (a),
   b) at least one organohydrogenpolysiloxane as component (b),
   c) at least one alkylsiloxane having at least one carbinol, carboxy or amino group as component (c),
   d) at least one condensation cure compound as component (d) and
   e) at least one addition cure precious metal catalyst as component (e);

wherein component (c) contains at least one compound of the formula:

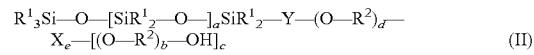

(II)

or

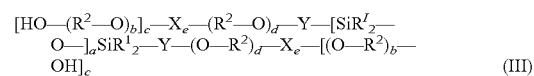

(III)

or

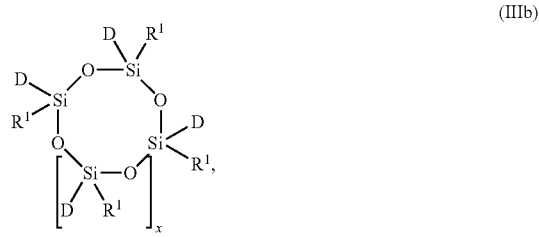

(IIIb)

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or —Y—(O—$R^2$)$_d$—X$_e$—[(O—$R^2$)$_b$—OH]$_c$ with at least one residue —Y—(O—$R^2$)$_d$—X$_e$—[(O—$R^2$)$_b$—OH]$_c$ per molecule, $1 \leq a \leq 10{,}000$, $0 \leq b \leq 500$, $1 \leq c \leq 6$, $0 \leq d \leq 500$, e is 0 or 1, and x is 0, 1, 2, 3, 4, 5 or 6.

2. The composition of claim 1, wherein the composition contains one or more adjuvants as component (f).

3. The composition of claim 1, wherein the composition contains the following components in the following amounts:
   a) 2.5 to 40 weight percent of component (a),
   b) 0.2 to 10 weight percent of component (b),
   c) 0.5 to 8 weight percent of component (c),
   d) 0.1 to 7 weight percent of component (a),
   e) 0.05 to 4 weight percent of component (e), based on elemental Pt, and
   f) 31 to 96.65 weight percent adjuvants as component (f),
wherein the components add up to 100 weight percent.

4. The composition of claim 3, wherein the adjuvant is selected from the group consisting of inert carrier materials, inhibitors, fillers, pigments or solvents.

5. A dental impression composition comprising:
   a) at least one polydiorganosiloxane having at least two olefinically unsaturated groups as component (a),
   b) at least one organohydrogenpolysiloxane as component (b),
   c) at least one alkylsiloxane having at least one carbinol, carboxy or amino group as component (c),
   d) at least one condensation cure compound as component (d) and
   e) at least one addition cure precious metal catalyst as component (e);
wherein component (c) contains at least one compound of the formula:

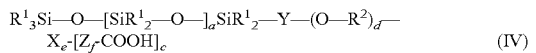
(IV)

or

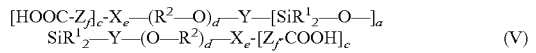
(V)

or

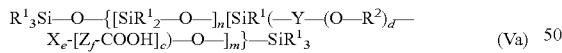
(Va)

or

(Vb)

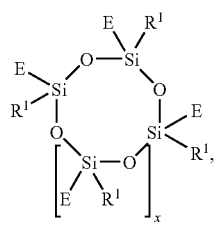

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 4 to 14 C-atoms, $R^2$ is a linear or branched alkylene group that may contain a carbonyl group with 1 to 8 C-atoms, E is $R^1$ or —Y—(O—$R^2$)$_d$—X$_e$-[Z$_f$-COOH]$_c$ with at least one residue —Y—(O—$R^2$)$_d$—X$_e$-[Z$_f$-COOH]$_c$ per molecule $1 \leq a \leq 10{,}000$, $1 \leq c \leq 6$, $0 \leq d \leq 500$, e is 0 or 1, f is 0 or 1, $0 \leq n \leq 500$, $0m \leq 100$ where m+n exceeds 5 and x is 0, 1, 2, 3, 4, 5 or 6.

6. The composition of claim 5, wherein the composition contains one or more adjuvants as component (f).

7. The composition of claim 5, wherein the composition contains the following components in the following amounts:
   a) 2.5 to 40 weight percent of component (a),
   b) 0.2 to 10 weight percent of component (b),
   c) 0.5 to 8 weight percent of component (c),
   d) 0.1 to 7 weight percent of component (d),
   e) 0.05 to 4 weight percent of component (e), based on elemental Pt, and
   f) 31 to 96.65 weight percent adjuvants as component (f),
wherein the components add up to 100 weight percent.

8. The composition of claim 7, wherein the adjuvant is selected from the group consisting of inert carrier materials, inhibitors, fillers, pigments or solvents.

9. A dental impression composition comprising:
   a) at least one polydiorganosiloxane having at least two olefinically unsaturated groups as component (a),
   b) at least one organohydrogenpolysiloxane as component (b),
   c) at least one alkylsiloxane having at least one carbinol, carboxy or amino group as component (c),
   d) at least one condensation cure compound as component (d) and
   e) at least one addition cure precious metal catalyst as component (e);
wherein component (c) contains at least one compound of the formula:

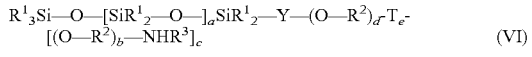
(VI)

or

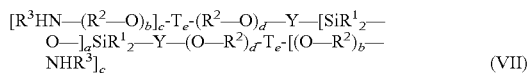
(VII)

or

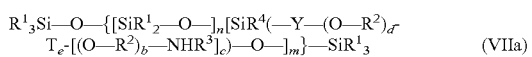
(VIIa)

or

(VIIb)

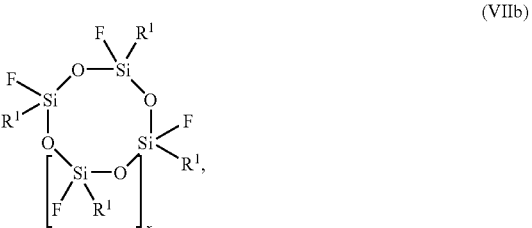

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ a linear or branched alkylene group that may contain a carbonyl group with 1 to 8 C-atoms, F is $R^1$ or $-Y-(O-R^2)_d-T_e-[(O-R^2)_b-NHR^3]_c$ with at least one residue $-Y-(O-R^2)_d-T_e-[(O-R^2)_{b-NHR}{}^3]_c$ per molecule, $R^3$ is a linear or branched alkyl or fluoroalkyl group with 1 to 8 C-atoms or a cycloalkyl or aryl group with 6 to 14 C-atoms, or H, $R^4$ is $R^1$ or methoxy or ethoxy, $1 \leq a \leq 10{,}000$, $0 \leq b \leq 10{,}000$, $1 \leq c \leq 6$, $0 \leq d \leq 500$, e is 0 or 1, $0 \leq n \leq 500$, $0 \leq m \leq 100$ where m+n exceeds 5 and x is 0, 1, 2, 3, 4, 5, or 6.

10. The composition of claim 9, wherein the composition contains one or more adjuvants as component (f).

11. The composition of claim 9, wherein the composition contains the following components in the following amounts:
a) 2.5 to 40 weight percent of component (a),
b) 0.2 to 10 weight percent of component (b),
c) 0.5 to 8 weight percent of component (c),
d) 0.1 to 7 weight percent of component (d),
e) 0.05 to 4 weight percent of component (e), based on elemental Pt, and
f) 31 to 96.65 weight percent adjuvants as component (f),
wherein the components add up to 100 weight percent.

12. The composition of claim 11, wherein the adjuvant is selected from the group consisting of inert carrier materials, inhibitors, fillers, pigments or solvents.

13. A two part dental impression system comprising parts A and B, wherein part A comprises:
a) at least one polydiorganosiloxane having at least two olefinically unsaturated groups as component (a).
b) at least one organohydrogenpolysiloxane as component (b), and
c) at least one alkylsiloxane having at least one carbinol, carboxy or amino group as component (c), wherein component (c) contains at least one compound of the formula:

$$R^1{}_3Si-O-[SiR^1{}_2-O-]_aSiR^1{}_2-Y-(O-R^2)_d-X_e-[(O-R^2)_b-OH]_c \quad (II)$$

or $$[HO-(R^2-O)_b]_c-X_e-(R^2-O)_d-Y-[SiR^1{}_2-O-]_aSiR^1{}_2-Y-(O-R^2)_d-X_e-[(O-R^2)_b-OH]_c \quad (III)$$

or $$R^1{}_3Si-O-\{[SiR^1{}_2-O-]_{n[SiR}{}^1(-Y-(O-R^2)_d-X_e-[(O-R^2)_b-OH]_c)-O-]_m\}-SiR^1{}_3 \quad (IIIa)$$

or (IIIb)

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with I to 8 C-atoms or a cycloalkyl or aryl group with 6 to 14 C-atoms, $R^2$ is a linear or branched alkylene group that may contain a carbonyl group with 1 to 8 C-atoms, D is $R^1$ or $-Y-(O-R^2)_d-X_e-[(O-R^2)_b-OH]_c$ with at least one residue $-Y-(O-R^2)_d-X_e-[(O-R^2)_b-OH]_c$ per molecule, $1 \leq a \leq 10{,}000$, $0 \leq b \leq 500$, $1 \leq c \leq 6$, $0 \leq d \leq 500$, e is 0 or 1, $0 \leq n \leq 500$, $0 \leq m \leq 100$ where m+n exceeds 5 and x is 0, 1, 2, 3, 4, 5 or 6;
and part B comprises:
d) at least one condensation cure component as component (d) and
e) at least one addition cure precious metal catalyst as component (e).

14. The composition according to claim 13, wherein part A contains the following components in the following amounts:
i) 8 to 25% by weight of component (a),
ii) 1 to 10 weight percent of component (b),
iii) 0.5 to 10 weight percent of component (c) and
iv) 55 to 90.5 weight percent of adjuvants,
wherein the components add up to 100 weight percent.

15. The composition according to claim 13, wherein part B contains the following components in the following amounts:
i) 0.5 to 10 weight percent of component (d),
ii) 0.1 to 5 weight percent of component (e), based on elemental Pt, and
iii) 85 to 99.4 weight percent of adjuvants,
wherein the components add up to 100 weight percent.

16. A method for the preparation of a dental impression composition, said method comprising the step of thoroughly mixing the following components in any order:
a) at least one polydiorganosiloxane having at least two olefinically unsaturated groups as component (a),
b) at least one organohydrogenpolysiloxane as component (b),
c) at least one alkylsiloxane having at least one carbinol, carboxy or amino group as component (c),
d) at least one condensation cure catalyst as component (d) and
e) at least one addition cure precious metal catalyst as component (e);
wherein component (c) contains at least one compound of the formula:

$$R^1{}_3Si-O-[SiR^1{}_2-O-]_aSiR^1{}_2-Y-(O-R^2)_d-X_e-[(O-R^2)_b-OH]_c \quad (II)$$

or $$[HO-(R^2-O)_b]_c-X_e-(R^2-O)_d-Y-[SiR^1{}_2-O-]_aSiR^1{}_2-Y-(O-R^2)_d-X_e-[(O-R^2)_b-OH]_c \quad (III)$$

or

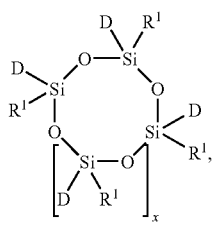
(IIIb)

wherein X is a linear or branched hydrocarbon or an aryl residue that may contain an oxygen atom and/or an ether group wit 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or $-Y-(O-R^2)_d-X_e-[(O-R^2)_b-OH]_c$ with at least one residue $-Y-(O-R^2)_d-X_e-[(O-R^2)_b-OH]_c$ per molecule, $1 \leq a \leq 10{,}000$, $0 \leq b \leq 500$, $1 \leq c \leq 6$, $0 \leq d \leq 500$, e is 0 or 1, and x is 0, 1, 2, 3, 4, 5 or 6.

17. A two part dental impression system comprising parts A and B, wherein part A comprises:
   a) at least one polydiorganosiloxane having at least two olefinically unsaturated groups as component (a),
   b) at least one organohydrogenpolysiloxane as component (b), and
   c) at least one alkylsiloxane having at least one carbinol, carboxy or amino group as component (c),
wherein component (c) contains at least one compound of the formula:

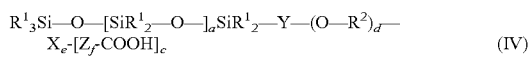
(IV)

or

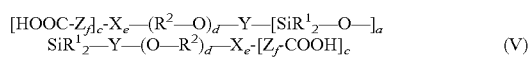
(V)

or

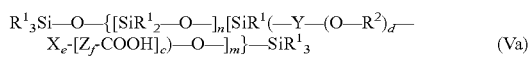
(Va)

or

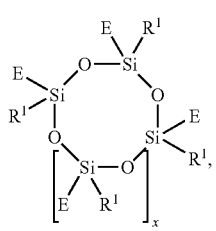
(Vb)

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 4 to 14 C-atoms, $R^2$ is a linear or branched alkylene group that may contain a carbonyl group with 1 to 8 C-atoms, E is $R^1$ or $-Y-(O-R^2)_d-X_e-[Z_f\text{-COOH}]_c$ with at least one residue $-Y-(O-R^2)_d-X_e-[Z_f\text{-COOH}]_c$ per molecule, $1 \leq a \leq 10{,}000$, $1 \leq c \leq 6$, $0 \leq d \leq 500$, e is 0 or 1, f is 0 or 1, $0 \leq n \leq 500$, $0 \leq m \leq 100$ where m+n exceeds 5 end x is 0, 1, 2, 3, 4, 5 or 6;

and part B comprises:
   d) at least one condensation cure component as component (d) and
   e) at least one addition cure precious metal catalyst as component (e).

18. The composition according to claim 17, wherein part A contains the following components in the following amounts:
   i) 8 to 25% by weight of component (a),
   ii) 1 to 10 weight percent of component (b),
   iii) 0.5 to 10 weight percent of component (c) and
   iv) 55 to 90.5 weight percent of adjuvants,
wherein the components add up to 100 weight percent.

19. The composition according to claim 17, wherein part B contains the following components in the following amounts:
   i) 0.5 to 10 weight percent of component (d),
   ii) 0.1 to 5 weight percent of component (e), based on elemental Pt, and
   iii) 85 to 99.4 weight percent of adjuvants,
wherein the components add up to 100 weight percent.

20. A method for the preparation of a dental impression composition, said method comprising the step of thoroughly mixing the following components in any order:
   a) at least one polydiorganosiloxane having at least two olefinically unsaturated groups as component (a),
   b) at least one organohydrogenpolysiloxane as component (b),
   c) at least one alkylsiloxane having at least one carbinol, carboxy or amino group as component (c),
   d) at least one condensation cure catalyst as component (d) and
   e) at least one addition cure precious metal catalyst as component (e);
wherein component (c) contains at least one compound of the formula:

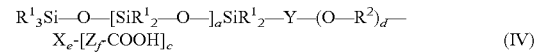
(IV)

or

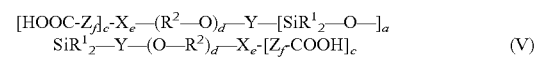
(V)

or

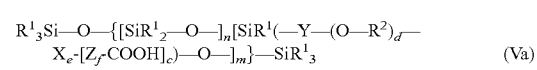
(Va)

or

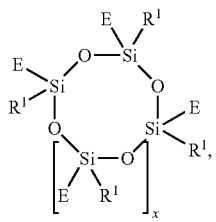
(Vb)

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 4 to 14 C-atoms, $R^2$ is a linear or branched alkylene group that may contain a carbonyl group with 1 to 8 C-atoms, E is $R^1$ or —Y—(O—$R^2$)$_d$—X$_e$-[Z$_f$-COOH]$_c$ with at least one residue —Y—(O—$R^2$)$_d$—X$_c$-[Z$_f$-COOH]$_c$ per molecule, $1 \leq a \leq 10{,}000$, $1 \leq c \leq 6$, $0 \leq d \leq 500$, e is 0 or 1, f is 0 or 1, $0 \leq n \leq 500$, $0 \leq m \leq 100$ where m+n exceeds 5 and x is 0, 1, 2, 3, 4, 5 or 6.

21. A two part dental impression system comprising parts A and B, wherein part A comprises:
    a) at least one polydiorganosiloxane having at least two olefinically unsaturated groups as component (a),
    b) at least one organohydrogenpolysiloxane as component (b), and
    c) at least one alkylsiloxane having at least one carbinol, carboxy or amino group as component (c),
wherein component (c) contains at least one compound of the formula:

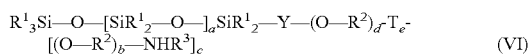
(VI)

or

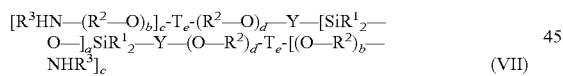
(VII)

or

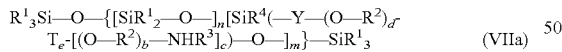
(VIIa)

or

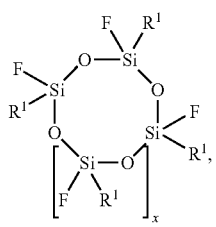
(VIIb)

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, F is $R^1$ or —Y—(O—$R^2$)$_d$—T$_e$—[(O—$R^2$)$_b$—NHR$^3$]$_c$ with at least one residue —Y—(O—$R^2$)$_d$—T$_e$—[(O—$R^2$)$_b$—NHR$^3$]$_c$ per molecule, $R^3$ is a liner or branched alkyl or fluoroalkyl group with 1 to 8 C-atoms or a cycloalkyl or aryl group with 6 to 14 C-atoms or H, $R^4$ or methoxy at ethoxy, $1 \leq a \leq 10{,}000$, $0 \leq b \leq 10{,}000$, $1 \leq c \leq 6$, $0 \leq d \leq 500$, e is 0 or 1, $0 \leq n \leq 500$, 0m 100 where m+n exceeds 5 and x is 0, 1, 2, 3, 4, 5 or 6;

and part B comprises:
    d) at least one condensation cure component as component (d) and
    e) at least one addition cure precious metal catalyst as component (e).

22. The composition according to claim 21, wherein part A contains the following components in the following amounts:
    i) 8 to 25% by weight of component (a),
    ii) 1 to 10 weight percent of component (b),
    iii) 0.5 to 10 weight percent of component (c) and
    iv) 55 to 90.5 weight percent of adjuvants.
wherein the components add up to 100 weight percent.

23. The composition according to claim 21, component wherein part B contains the following component in the following amounts:
    i) 0.5 to 10 weight percent of component (d),
    ii) 0.1 to 5 weight percent of component (e), based on elemental Pt, and
    iii) 85 to 99.4 weight percent of adjuvants,
wherein the components add up to 100 weight percent.

24. The method for the preparation of a dental impression composition, said method comprising the step of thoroughly mixing the following components in any order:
    a) at least one polydiorganosiloxane having at least two olefinically unsaturated groups as component (a),
    b) at least one organohydrogenpolysiloxane as component (b),
    c) at Least one alkylsiloxane having at least one carbinol, carboxy or amino group as component (c),
    d) at least one condensation cure catalyst as component (d) and
    e) at least one addition cure precious metal catalyst as component (e);
wherein component (c) contains at least one compound of the formula:

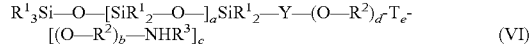
(VI)

or

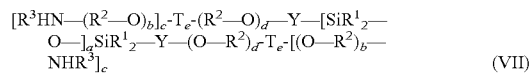
(VII)

or

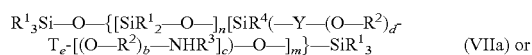
(VIIa) or

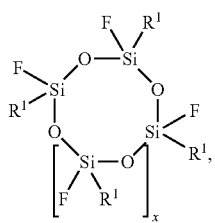

(VIIb)

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, F is $R^1$ or $-Y-(O-R^2)_d-T_e-[(O-R^2)_b-NHR^3]_c$ with at least one residue $-Y-(O-R^2)_d-T_e-[(O-R^2)_b-NHR^3]_c$ per molecule, $R^3$ is a linear or branched alkyl or fluoroalkyl group with 1 to 8 C-atoms or a cycloalkyl or aryl group with 6 to 14 C-atoms or H, $R^4$ is $R^1$ or methoxy or ethoxy, $1 \leq a \leq 10{,}000$, $0 \leq b \leq 10{,}000$, $1 \leq c \leq 6$, $0 \leq d \leq 500$, e is 0 or 1, $0 \leq n \leq 500$, $0 \leq m \leq 100$ where m+n exceeds 5 and x is 0, 1, 2, 3, 4, 5 or 6.

* * * * *

UNITED STATES PATENT AND TRADEMARK OFFICE
CERTIFICATE OF CORRECTION

PATENT NO. : 7,572,842 B2  
APPLICATION NO. : 10/566926  
DATED : August 11, 2009  
INVENTOR(S) : Joachim W. Zech It is certified that error appears in the above-identified patent and that said Letters Patent is hereby corrected as shown below:

Column 2  
Line 15, delete "generelly" and insert -- generally --, therefor.

Column 3  
Line 16, delete "compositon" and insert -- composition --, therefor.

Column 4  
Line 30, delete "consituents" and insert -- constituents --, therefor.  
Line 34, delete "subsituent" and insert -- substituent --, therefor.  
Line 34, delete "consituents" and insert -- constituents --, therefor.  
Line 51, delete "hereroaromatic" and insert -- heteroaromatic --, therefor.

Column 5  
Line 31, delete "polydipersity" and insert -- polydispersity --, therefor.

Column 6  
Line 47-48, delete "polyalkyxsiloxanes" and insert -- polyalkylsiloxanes --, therefor.

Column 7  
Line 41, delete "10.000," and insert -- 10,000, --, therefor.

Column 8  
Line 12, delete "10.000," and insert -- 10,000, --, therefor.  
Line 52, delete "10.000," and insert -- 10,000, --, therefor.  
Line 52, delete "10.000," and insert -- 10,000, --, therefor.

Column 9  
Line 24, delete "10.000," and insert -- 10,000, --, therefor.

Signed and Sealed this

Tenth Day of August, 2010

David J. Kappos  
*Director of the United States Patent and Trademark Office*

Column 10
Line 53, delete "allypolylglycol" and insert -- allylpolyglycol --, therefor.

Column 15
Line 2, delete "preffered" and insert -- preferred --, therefor.
Line 39, delete "10.000," and insert -- 10,000, --, therefor.

Column 19
Line 16, delete "exeed" and insert -- exceed --, therefor.

Column 20
Line 34, delete "reation" and insert -- reaction --, therefor.
Line 53, delete "crosslinging" and insert -- crosslinking --, therefor.

Column 21
Line 26, delete "tetramethyldivinyidisiloxane." and insert -- tetramethyldivinyldisiloxane. --, therefor.

Column 22
Line 18, delete "perfluoralkylated" and insert -- perfluoroalkylated --, therefor.
Line 59, delete "moleculer" and insert -- molecular --, therefor.

Column 23
Line 57, delete "comcomponent" and insert -- component --, therefor.

Column 24
Line 18, delete "acording" and insert -- according --, therefor.
Line 44, delete "10.000," and insert -- 10,000, --, therefor.
Line 58, delete "weigt" and insert -- weight --, therefor.
Line 59, delete "perent" and insert -- percent --, therefor.
Line 61, delete "(e," and insert -- (f), --, therefor.

Column 25
Line 12, delete "it" and insert -- is --, therefor.

Column 26
Line 26, delete "adental" and insert -- a dental --, therefor.

Column 27
Line 39, delete "seperation" and insert -- separation --, therefor.
Line 53, delete "PVC" and insert -- Pt/C --, therefor.

Column 30
Line 26, delete "puffy-like" and insert -- putty-like --, therefor.
Line 51, Claim 1, the text to insert should read as follows:

$$[HO-(R^2-O)_b]_c-X_e-(R^2-O)_d-Y-[SiR^1{}_2-O-]_aSiR^1{}_2-Y-(O-R^2)_d-X_e-[(O-R^2)_b-OH]_c$$

CERTIFICATE OF CORRECTION (continued)

U.S. Pat. No. 7,572,842 B2

Column 31
Line 20, Claim 3, delete "(a)," and insert -- (d), --, therefor.

Column 32
Line 10, Claim 5, delete "molecule" and insert -- molecule, --, therefor.
Line 10, Claim 5, delete "1 ," and insert -- 1, --, therefor.
Line 11, Claim 5, delete "0m≦100" and insert -- $0 \leqq m \leqq 100$ --, therefor.

Column 33
Line 8, Claim 9, delete "$R^2$" and insert -- $R^2$ is --, therefor.
Line 11-12, Claim 9 the text to insert should read as follows:

$$-Y-(O-R^2)_d-T_e-[(O-R^2)_b-NHR^3]_c$$

Line 15, Claim 9, delete "C-atoms," and insert -- C-atoms --, therefor.
Line 43, Claim 13, delete "(a)." and insert -- (a), --, therefor.
Line 66-67, Claim 13, the text to insert should read as follows:

$$R^1{}_3Si-O-\{[SiR^1{}_2-O-]_n\,[SiR^1(-Y-(O-R^2)_d-X_e-[(O-R^2)_b-OH]_c)-O-]_m\}-SiR^1{}_3$$

Column 34
Line 18, Claim 13, delete "I" and insert -- 1 --, therefor.

Column 35
Line 17, Claim 16, delete "wit" and insert -- with --, therefor.

Column 36
Line 10, Claim 17, delete "end" and insert -- and --, therefor.

Column 38
Line 9, Claim 21, delete "liner" and insert -- linear --, therefor.
Line 11, Claim 21, delete "$R^4$" and insert -- $R^4$ is $R^1$ --, therefor.
Line 11 Claim 21, delete "at" and insert -- or --, therefor.
Line 14, Claim 21, delete "0m 100" and insert -- $0 \leqq m \leqq 100$ --, therefor.
Line 27, Claim 22, delete "adjuvants." and insert -- adjuvants, --, therefor.
Line 30, Claim 23, after "claim 21," delete "component".
Line 47, Claim 24, delete "Least" and insert -- least --, therefor.